United States Patent [19]

Herrmann et al.

[11] Patent Number: 5,194,382
[45] Date of Patent: Mar. 16, 1993

[54] METHOD FOR INCREASING THE ENZYMATIC REACTIVITY OF β-GALACTOSIDASE BY ADDITION OF A CYANATE, THIOCYANATE, AZIDE, OR THIOSULFATE COMPOUND

[75] Inventors: Rupert Herrmann; Hans-Joachim Guder, both of Weilheim; Martina Junius-Comer, Iffeldorf, all of Fed. Rep. of Germany

[73] Assignee: Boehringer Mannheim GmbH, Mannheim-Waldhof, Fed. Rep. of Germany

[21] Appl. No.: 609,242

[22] Filed: Nov. 5, 1990

[30] Foreign Application Priority Data

Nov. 14, 1989 [DE] Fed. Rep. of Germany ....... 3937880
Mar. 12, 1990 [DE] Fed. Rep. of Germany ....... 4007836

[51] Int. Cl.$^5$ ................................................ C12N 9/38
[52] U.S. Cl. .................................... 435/207; 435/7.3; 435/7.4; 435/7.94
[58] Field of Search ................. 435/207, 7.3, 7.4, 7.94

[56] References Cited

U.S. PATENT DOCUMENTS 4,891,313  1/1990  Berger et al. ...................... 435/7.94

FOREIGN PATENT DOCUMENTS 0049475  4/1982  European Pat. Off. .

OTHER PUBLICATIONS

Sigma Catalogue, 1989 p. 499.
Kirk-Ohmer, Encyclopedia of Chemical Technology, vol.s 17 & 22, pp. 611–656, 974–989 respectively, 3rd Ed., Wiley Interscience 1979.
Chebotareva et al., "Processing of Color Silver Halide Photographic Materials", *Chemical Abstracts*, 91:81554n, 1979.
Klose et al., "Stabilized Reagent for Detecting Hydrogen Peroxide", *Chemical Abstracts* 98:140126u, 1983.
Zhao et al., "Color Reaction of Zinc with Thiocyanate and Brilliant Green . . . ", *Chemical Abstracts*, 103:152886b, 1985.

*Primary Examiner*—Douglas W. Robinson
*Assistant Examiner*—Marian C. Knode
*Attorney, Agent, or Firm*—Felfe & Lynch

[57] ABSTRACT

In order to increase the enzymatic reactivity of β-galactosidase, an azide, thiocyanate, cyanate and/or thiosulphate is added to the reaction mixture.

17 Claims, No Drawings

METHOD FOR INCREASING THE ENZYMATIC REACTIVITY OF β-GALACTOSIDASE BY ADDITION OF A CYANATE, THIOCYANATE, AZIDE, OR THIOSULFATE COMPOUND

FIELD OF THE INVENTION

The invention concerns a method for increasing the enzymatic reactivity of β-galactosidase as well as a test kit which contains β-galactosidase and a substrate which can be converted by β-galactosidase.

BACKGROUND AND PRIOR ART

β-galactosidase is a conventional marker enzyme which is used in immunological test procedures. However, in most cases a considerable measurement time is required to carry out such test procedures which under certain circumstances, e.g. in determinations which have to be carried out quickly following accidents and in medical emergency situations, can cause a life-threatening delay in the onset of the necessary therapeutic procedures. There is therefore a great need to shorten these reaction times.

Moreover, the antibodies needed for such immunological test procedures can usually only be produced by means of extremely complicated procedures which is another reason to try to keep the amount of antibodies required for such a test as small as possible. Since, however, when the amount of antibodies is decreased there are also less marker enzymes present in the enzyme-immunoassay, the sensitivity of the detection reaction also decreases.

On the other hand, it is also possible to use a smaller amount of the substance to be examined by increasing the sensitivity of such immunological test procedures. This is of particular importance when only a limited amount of the substance to be examined is available and a multitude of analytical tests is to be carried out on it.

It is therefore the aim of the invention to overcome the previously-mentioned disadvantages and to provide a test method with an increased sensitivity.

DETAILED DESCRIPTION OF THE PREFERRED EMBODIMENTS

This object is achieved according to the present invention by a method for increasing the enzymatic reactivity of β-galactosidase which is characterized in that the salt or salts of azides, thiocyanates, cyanates and/or thiosulphates are added to the reaction mixtures. Surprisingly, it turned out that the addition of such salts leads to an acceleration of the enzymatic reactivity of β-galactosidase which means an increase in the sensitivity of such enzymatic test methods in which this enzyme is used. The increase in the enzymatic reactivity of the β-galactosidase reactions obtained with the accelerator salts mentioned previously, in particular the hydrolytic cleavage activity of this enzyme, is especially surprising since other hydrolases such as e.g. glucosidase or alkaline phosphatase are not stimulated but are even slightly inhibited when these accelerator salts are used in the same amounts (as compared with the β-galactosidase test).

The thiosulphate, cyanate and thiocyanate salts are preferred among the accelerator salts since they achieve the effect according to the present invention with the least amounts. The range which is particularly suitable is between 0.5 and 10 mmol/l. Larger additions do not cause a further improvement. 0.8 to 5 mmol/l is preferred. With azide the suitable range is between 50 and 200 mmol/l. Also in this case higher concentrations are still effective but are not better. 80 to 150 mmol/l is preferably used. The type of cation present in these salts is of no importance for achieving the effect according to the present invention. It has, however, proven to be expedient to use the cations lithium, sodium, potassium, calcium, magnesium and ammonium which are usually present in biochemical reactions.

The usual substrates known to the expert are used in the method according to the present invention for the β-galactosidase cleavage. In particular, it is expedient to use such substrates which have a photometrically measurable or a radioactive group. It has turned out to be advantageous to use resorufin-β-D-galactopyranoside, chlorophenol-red-β-D-galactopyranoside, 2-nitrophenyl-β-D-galactopyranoside and/or 2-chloro-4-nitrophenyl-β-D-galactopyranoside as well as 2-cyano-4-nitrophenyl-β-D-galactopyranoside and 2-trifluoromethyl-4-nitrophenyl-β-D-galactopyranoside (produced according to the German Patent application P 40 21 063.4) as substrate.

Surprisingly, it has also turned out that the increase in the enzymatic reactivity of β-galactosidase according to the present invention is most pronounced when the amount of enzyme used is as small as possible and thus the cleavage of substrate in the absence of accelerator is extremely slow. Finally, it has also turned out that the addition of accelerator salt does not lead to a non-enzymatic hydrolysis of the substrate and the effect according to the present invention is therefore neither caused by a background reaction nor is it overlapped by one.

The invention also provides a test kit which contains β-galactosidase as marker enzyme, a substrate which can be converted by β-galactosidase as well as an accelerator in the form of an azide, thiocyanate, cyanate and/or thiosulphate salt.

The invention is elucidated further by the following examples.

EXAMPLE 1

Determination of β-galactosidase with
2-chloro-4-nitrophenyl-β-D-galactopyranoside
(CNPG) as substrate Reagent:
   0.1 mmol/l CNPG in buffer I
Buffer 1:
   0.05 mol/l potassium phosphate buffer, pH 7.0
   0.16 mmol/l magnesium chloride
Sample:
   β-galactosidase (specific activity ca 600 U/mg protein at 37° C. determined using 2-nitrophenyl-β-D-galactoside as substrate, EC 3.2.1.23, The determination is carried out in such a way that reagent and sample, if desired with addition of amplifier, are added to buffer I and the time-course of the absorbance is determined at 405 nm. The results are shown in Tables I, II, III, IIIa and IIIb.

TABLE I

Results for potassium thiocyanate as amplifier, enzyme concentration 0.3 μg/ml
Measurement 1: without amplifier
Measurement 2: with 1 mmol/l potassium thiocyanate

| t (min) | measurement 1 | measurement 2 | amplification factor |
| --- | --- | --- | --- |
| 1 | 0.048 | 0.084 | 1.75 |
| 3 | 0.084 | 0.254 | 3.02 |

TABLE I-continued

Results for potassium thiocyanate as amplifier, enzyme
concentration 0.3 μg/ml
Measurement 1: without amplifier
Measurement 2: with 1 mmol/l potassium thiocyanate

| t (min) | measurement 1 | measurement 2 | amplification factor |
|---|---|---|---|
| 5 | 0.094 | 0.411 | 4.37 |
| 7 | 0.098 | 0.555 | 5.66 |
| 9 | 0.100 | 0.685 | 6.85 |
| 11 | 0.101 | 0.802 | 7.94 |
| 13 | 0.102 | 0.906 | 8.88 |

TABLE II

Results for sodium azide as amplifier, enzyme
concentration 0.17 μg/ml
Measurement 1: without amplifier
Measurement 2: with 0.1 mol/l sodium azide

| t (min) | measurement 1 | measurement 2 | amplification factor |
|---|---|---|---|
| 1 | 0.15 | 0.26 | 1.73 |
| 3 | 0.35 | 0.58 | 1.66 |
| 5 | 0.53 | 0.84 | 1.58 |
| 7 | 0.69 | 1.05 | 1.52 |
| 9 | 0.83 | 1.20 | 1.44 |
| 11 | 0.95 | 1.32 | 1.39 |
| 13 | 1.07 | 1.39 | 1.30 |

TABLE III

Results for sodium azide as amplifier, enzyme
concentration 0.017 μg/ml
Measurement 1: without amplifier
Measurement 2. with 0.1 mol/l sodium azide

| t [min] | measurement 1 | measurement 2 |
|---|---|---|
| 0.5 | 0.0005 | 0.0035 |
| 3.5 | 0.001 | 0.009 |
| 5 | 0.001 | 0.011 |
| 7 | 0.001 | 0.015 |
| 9 | 0.001 | 0.019 |
| 11 | 0.001 | 0.023 |

TABLE IIIa

Results for sodium thiosulphate as amplifier, enzyme
concentration 0.17 μg/ml
Measurement 1: without amplifier
Measurement 2: with 1 mmol/l sodium thiosulphate

| t [min] | measurement 1 | measurement 2 |
|---|---|---|
| 0.5 | 0.03 | 0.05 |
| 3 | 0.07 | 0.16 |
| 5 | 0.08 | 0.25 |
| 10 | 0.09 | 0.47 |
| 20 | 0.095 | 0.83 |

TAABLE IIIb

Results for potassium cyanate as amplifier, enzyme
concentration: 0.17 μg/ml
Measurement 1: without amplifier
Measurement 2: with 1 mmol/l potassium cyanate

| t [min] | measurement 1 | measurement 2 |
|---|---|---|
| 1 | 0.040 | 0.045 |
| 2 | 0.060 | 0.075 |
| 3 | 0.070 | 0.100 |
| 4 | 0.075 | 0.115 |
| 5 | 0.080 | 0.130 |
| 6 | 0.085 | 0.150 |
| 10 | 0.090 | 0.190 |
| 15 | 0.095 | 0.240 |

EXAMPLE 2

Determination of β-galactosidase with
resorufin-β-galactoside (RG) as substrate

Reagent:
0.04 mmol/l RG in buffer I
The determination is carried out as described in Example 1. The results are shown in Tables IV to VI.

TABLE IV

Results for potassium thiocyanate as amplifier, enzyme
concentration 0.17 μg/ml
Measurement 1: without amplifier
Measurement 2: with 1 mmol/l KSCN

| t [min] | measurement 1 | measurement 2 |
|---|---|---|
| 1 | 0.23 | 0.27 |
| 3 | 0.48 | 0.58 |
| 5 | 0.68 | 0.85 |
| 7 | 0.86 | 1.10 |
| 9 | 1.02 | 1.28 |
| 11 | 1.16 | 1.46 |
| 13 | 1.24 | 1.58 |

TABLE V

Results for potassium thiocyanate as amplifier, enzyme
concentration 0.017 μg/ml
Measurement 1: without amplifier
Measurement 2: with 1 mmol/l KSCN

| t [min] | measurement 1 | measurement 2 |
|---|---|---|
| 1 | 0.012 | 0.018 |
| 3 | 0.030 | 0.045 |
| 5 | 0.045 | 0.074 |
| 7 | 0.055 | 0.102 |
| 9 | 0.065 | 0.132 |
| 11 | 0.070 | 0.160 |
| 13 | 0.074 | 0.190 |

TABLE VI

Results for sodium azide as amplifier, enzyme
concentration 0.17 μg/ml
Measurement 1: without amplifier
Measurement 2: with 0.1 mol/l NaN$_3$

| t [min] | measurement 1 | measurement 2 |
|---|---|---|
| 1 | 0.08 | 0.14 |
| 3 | 0.18 | 0.33 |
| 5 | 0.25 | 0.50 |
| 7 | 0.32 | 0.66 |
| 9 | 0.36 | 0.80 |
| 11 | 0.40 | 0.93 |
| 12.5 | 0.42 | 1.02 |

EXAMPLE 3

Determination of β-galactosidase with
chlorophenol-red-β-galactoside (CPG) as substrate Reagent:
0.1 mmol/l CPG in buffer I
The determination is carried out as described in Example 1. The results are shown in Tables VII, VIII and IX.

TABLE VII

Results for potassium thiocyanate as amplifier, enzyme
concentration 0.17 μg/ml
Measurement 1: without amplifier
Measurement 2: with 1 mmol/l KSCN

| t [min] | measurement 1 | measurement 2 |
|---|---|---|
| 5 | 0.37 | 0.46 |
| 10 | 0.68 | 0.88 |
| 15 | 0.98 | 1.26 |

TABLE VIII

Results for potassium thiocyanate as amplifier, enzyme
concentration 0.017 µg/ml
Measurement 1: without amplifier
Measurement 2: with 1 mmol/l KSCN

| t [min] | measurement 1 | measurement 2 |
|---|---|---|
| 5 | 0.022 | 0.034 |
| 10 | 0.032 | 0.068 |
| 15 | 0.040 | 0.104 |
| 20 | 0.044 | 0.144 |
| 25 | 0.046 | 1.184 |

TABLE IX

Results for sodium azide as amplifier, enzyme
concentration 0.17 µg/ml
Measurement 1: without amplifier
Measurement 2: with 0.1 mol/l NaN$_3$

| t [min] | measurement 1 | measurement 2 |
|---|---|---|
| 5 | 0.26 | 0.63 |
| 10 | 0.50 | 1.18 |

We claim:

1. A method for accelerating reaction between β-galactosidase and a β-galactosidase substrate comprising adding an amount of a compound selected from the group consisting of an azide containing compound, thiocyanate containing compound, a cyanate containing compound, and a thiosulphate containing compound to a reaction mixture containing β-galactosidase and a β-galactosidase substrate sufficient to accelerate the reaction therebetween as compared to reaction between β-galactosidase and said β-galactosidase in the absence of said compound.

2. The method of claim 1, wherein said compound is a lithium, sodium, potassium, calcium, magnesium or ammonium salt.

3. The method of claim 1, wherein said compound is a thiosulphate containing compound, a cyanate containing compound or a thiocyanate containing compound.

4. The method of claim 3, wherein said compound is present in an amount ranging from 0.5 to 10 mmol/l.

5. The method of claim 4, wherein said compound is present in an amount ranging from 0.8 to 5 mmol/l.

6. The method of claim 1, wherein said compound is an azide containing compound.

7. The method of claim 6, wherein said azide containing compound is present in an amount ranging from 50 to 200 mmol/l.

8. The method of claim 7, wherein said azide containing compound is present in an amount ranging from 80 to 150 mmol/l.

9. The method of claim 1, wherein said compound is potassium thiocyanate, sodium azide, sodium thiosulphate, or potassium cyanate.

10. The method of claim 1, wherein said compound is potassium thiocyanate.

11. The method of claim 1, wherein said compound is sodium azide.

12. The method of claim 1, wherein said compound is sodium thiosulphate.

13. The method of claim 1, wherein said compound is potassium cyanate.

14. A test kit useful in an immunoassay comprising a separate portion of each of (i) β-galactosidase, (ii) a β-galactosidase substrate and (iii) an amount of a compound selected from the group consisting of an azide containing compound, a thiocyanate containing compound, a cyanate containing compound, and a thiosulphate containing compound sufficient to accelerate reaction between β-galactosidase and β-galactosidase substrate, wherein said compound is present in said test kit (a) as a separate portion, (b) combined with the separate portion of said β-galactosidase substrate, or (c) combined with the separate portion of β-galactosidase.

15. The test kit of claim 14, wherein said compound is present as a separate portion.

16. The test kit of claim 14, wherein said compound is combined with said β-galactosidase or said substrate.

17. A method for improving reaction between β-galactosidase and a substrate selected from the group consisting of resorufin-β-D-galactopyranoside, chlorophenol-red-β-D-galactopyranoside, 2-nitrohpeny-β-D-galactopyranoside and 2-chloro-4-nitrophenyl-β-D-galactopyranoside comprising combining β-galactosidase and said substrate in a reaction mixture with an amount of a compound selected from the group consisting of an azide containing compound, thiocyanate containing compound, a cyanate containing compound, and a thiosulphate containing compound sufficient to increase enzymatic activity of β-galactosidase on said substrate.

* * * * *